(12) United States Patent
Davis et al.

(10) Patent No.: US 10,219,732 B2
(45) Date of Patent: Mar. 5, 2019

(54) BLOOD GLUCOSE MANAGEMENT SYSTEM

(71) Applicant: POPS! Diabetes Care, Inc., Stillwater, MN (US)

(72) Inventors: Daniel W. Davis, Hugo, MN (US); Chandler Stormo, Stillwater, MN (US); Curtis J. Christensen, Stillwater, MN (US); Erik D. Davis, St. Louis Park, MN (US); Lonny Stormo, Stillwater, MN (US)

(73) Assignee: POPS! Diabetes Care, Inc., Stillwater, MN (US)

( * ) Notice: Subject to any disclaimer, the term of this patent is extended or adjusted under 35 U.S.C. 154(b) by 0 days.

(21) Appl. No.: 15/122,284

(22) PCT Filed: Aug. 27, 2016

(86) PCT No.: PCT/US2016/049160
§ 371 (c)(1),
(2) Date: Aug. 29, 2016

(87) PCT Pub. No.: WO2017/040352
PCT Pub. Date: Mar. 9, 2017

(65) Prior Publication Data
US 2017/0143244 A1 May 25, 2017

Related U.S. Application Data

(60) Provisional application No. 62/211,278, filed on Aug. 28, 2015.

(51) Int. Cl.
*A61B 5/157* (2006.01)
*A61B 50/30* (2016.01)
(Continued)

(52) U.S. Cl.
CPC .......... *A61B 5/157* (2013.01); *A61B 5/14532* (2013.01); *A61B 5/150022* (2013.01);
(Continued)

(58) Field of Classification Search
CPC . A61B 5/157; A61B 50/3001; A61B 5/14532; A61B 5/150251;
(Continued)

(56) References Cited

U.S. PATENT DOCUMENTS 5,120,643 A * 6/1992 Ching .............. G01N 33/54366
422/408
6,315,738 B1 * 11/2001 Nishikawa ....... A61B 5/150022
600/583
(Continued)

FOREIGN PATENT DOCUMENTS

EP 1139873 A1 10/2001
WO 2013004823 A1 1/2013
(Continued)

OTHER PUBLICATIONS

International Patent Application No. PCT/US2016/049160, International Search Report and Written Opinion dated Jan. 23, 2017, 15 pages.
(Continued)

*Primary Examiner* — Jill A Warden
*Assistant Examiner* — Jacqueline Brazin
(74) *Attorney, Agent, or Firm* — Fredrikson & Byron, P.A.

(57) ABSTRACT

A biological property testing device includes a base comprising a primary surface extending in a base plane, and a first lancet station supported by the base. A first test strip channel provided in the base can have a main channel portion extending generally parallel with the base plane, and an angled channel portion that forms an angle with the main
(Continued)

channel portion between 5 degrees and 90 degrees. The first test strip channel can house a biological test strip oriented so that a meter connecting end of the biological test strip is adjacent to the main channel portion and a sample end of the biological test strip is adjacent to the angled channel portion.

26 Claims, 19 Drawing Sheets

(51) Int. Cl.
    *A61B 5/151*     (2006.01)
    *A61B 5/15*     (2006.01)
    *A61B 5/145*     (2006.01)
    *G01N 33/487*     (2006.01)

(52) U.S. Cl.
    CPC ...... *A61B 5/15087* (2013.01); *A61B 5/15146* (2013.01); *A61B 5/15151* (2013.01); *A61B 5/150251* (2013.01); *A61B 5/150305* (2013.01); *A61B 5/150358* (2013.01); *A61B 5/150572* (2013.01); *A61B 50/3001* (2016.02); *G01N 33/4875* (2013.01); *A61B 2562/0295* (2013.01); *A61B 2562/18* (2013.01)

(58) Field of Classification Search
    CPC ........ A61B 5/150305; A61B 5/150358; A61B 5/15087; A61B 5/15146
    USPC .......................................................... 422/410
    See application file for complete search history.

(56) References Cited

U.S. PATENT DOCUMENTS

| | | | |
|---|---|---|---|
| 8,647,357 B2 | 2/2014 | Christensen et al. | |
| 8,815,175 B2* | 8/2014 | Bryer ................. | A61B 5/14532 422/410 |
| 9,237,866 B2 | 1/2016 | Christensen et al. | |
| 2014/0188002 A1* | 7/2014 | Close ................. | A61M 5/16804 600/581 |
| 2014/0309558 A1* | 10/2014 | Fletcher ........... | A61B 5/150305 600/583 |
| 2016/0324464 A1 | 11/2016 | Christensen et al. | |
| 2016/0324481 A1 | 11/2016 | Christensen et al. | |
| 2016/0328527 A1 | 11/2016 | Christensen et al. | |

FOREIGN PATENT DOCUMENTS

| | | |
|---|---|---|
| WO | 2014179171 A1 | 11/2014 |
| WO | WO 2014179171 * | 11/2014 |

OTHER PUBLICATIONS

International Patent Application No. PCT/US2016/049160, Invitation to Pay Additional Fees and Partial Search Report dated Dec. 2, 2016, 6 pages.

* cited by examiner

BLOOD GLUCOSE MANAGEMENT SYSTEM

RELATED APPLICATIONS

This application is a 35 U.S.C. 371 national stage filing from International Application No. PCT/US2016/049160, filed Aug. 27, 2016, which claims the benefit of U.S. Provisional Patent Application No. 62/211,278, filed Aug. 28, 2015, the entire contents of which are incorporated herein by reference.

BACKGROUND

Managing a patient's blood glucose levels can be challenging. Generally, a patient must provide a blood sample to a meter multiple times each day and must self-assess based on the blood glucose measurements and associated trends, along with other factors he/she thinks may be influencing the measurements. The patient typically provides the blood sample by lancing his/her finger (or other body part) with a lancing device, applying the blood sample to a separate test strip, and introducing the test strip to the meter-three separate components are required. This arrangement often means patients are less likely to test their blood glucose levels as often as recommended and that any conclusions drawn from the measurement are based on incomplete information. Moreover, it can be difficult to provide relevant blood glucose information to others for whom accessing such information may be beneficial.

SUMMARY

In general, this disclosure is directed to a biological property testing apparatus. Some exemplary embodiments of the biological property testing apparatus can include a testing module. The testing module can include a base comprising a primary surface extending in a base plane, a lancet station supported by the base and having a lancet, and a test section. The test section can have a test strip channel.

In certain embodiments, the test strip channel can have a main channel portion extending generally parallel with the base plane, and an angled channel portion that forms an angle with the main channel portion between 5 degrees and 90 degrees. The test strip channel can house a biological test strip oriented so that a meter connecting end of the biological test strip is adjacent to the main channel portion and a sample end of the biological test strip is adjacent to the angled channel portion.

According to some embodiments, the test section includes a sample cavity. The biological property testing device can have a cover tab coupled to the base and movable from a covered position to an uncovered position. A moisture barrier can seal off the sample cavity when the cover tab is in the covered position and not seal off the sample cavity when the cover tab is in the uncovered position. A sterile barrier can seal off the lancet aperture when the cover tab is in the covered position and not seal off the lancet aperture when the cover tab is in the uncovered position.

The biological property testing apparatus according to illustrative embodiments can have a meter module removably attachable to its housing. The meter module can receive the meter connecting end of the biological test strip when the testing module and the meter module are attached to the housing.

Some embodiments provide a housing that facilitates use of conventional biological test strips in new biological property testing devices and apparatuses. One or more conventional biological test strips can be assembled into a base that also includes a corresponding number of lancet stations. The sample ends of the biological test strips can be positioned proximate to the lancets of the lancet stations to minimize the distance a patient must move his/her lanced finger or other body part. The biological test strips can be bent so that the sample ends are positioned to easily receive a biological sample from the patient. The meter connecting ends of the biological test strips can extend out of the housing and into a meter module that includes electronics for measuring a biological property of the biological sample provided by the patient.

In some embodiments, prior to use, the testing module keeps the lancet in the lancet station sterile and keeps the biological test strip generally free from moisture. A sealant can be applied to prevent moisture from entering a sample cavity of the testing module through the end of the testing module through which the meter connecting end of the biological test strip extends. The testing module can include a cover tab that prevents moisture from contacting the biological test strip and keeps the lancet sterile prior to use. In many embodiments, a moisture barrier is provided on an underside of the cover tab to prevent moisture from contacting the biological test strip prior to use. In some embodiments, a desiccant can be included proximate to the sample end of the biological test strip prior to use. In many embodiments, a sterile barrier is provided on an underside of the cover tab to keep the lancet sterile prior to use.

The details of one or more examples are set forth in the accompanying drawings and the description below. Other features, objects, and advantages will be apparent from the description and drawings, and from the claims.

DETAILED DESCRIPTION

Figure 1:
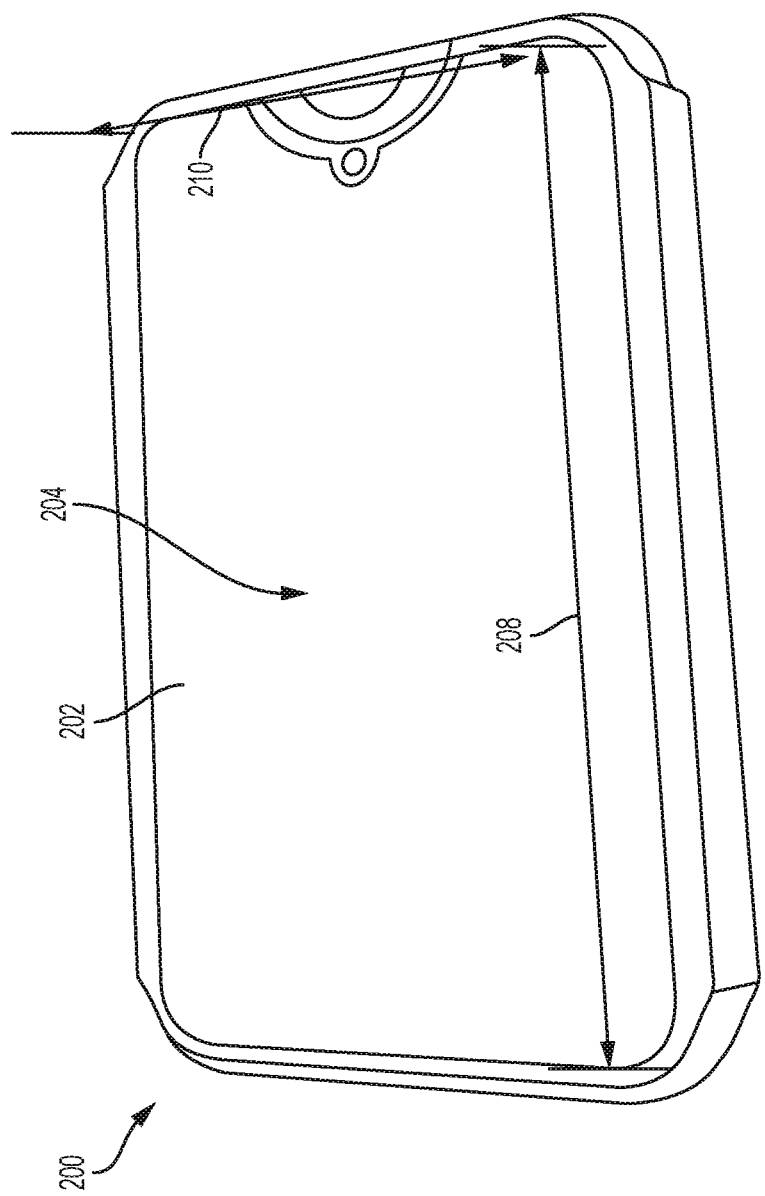
FIG. 1 shows a biological property testing apparatus according to an exemplary embodiment.
Figure 2:
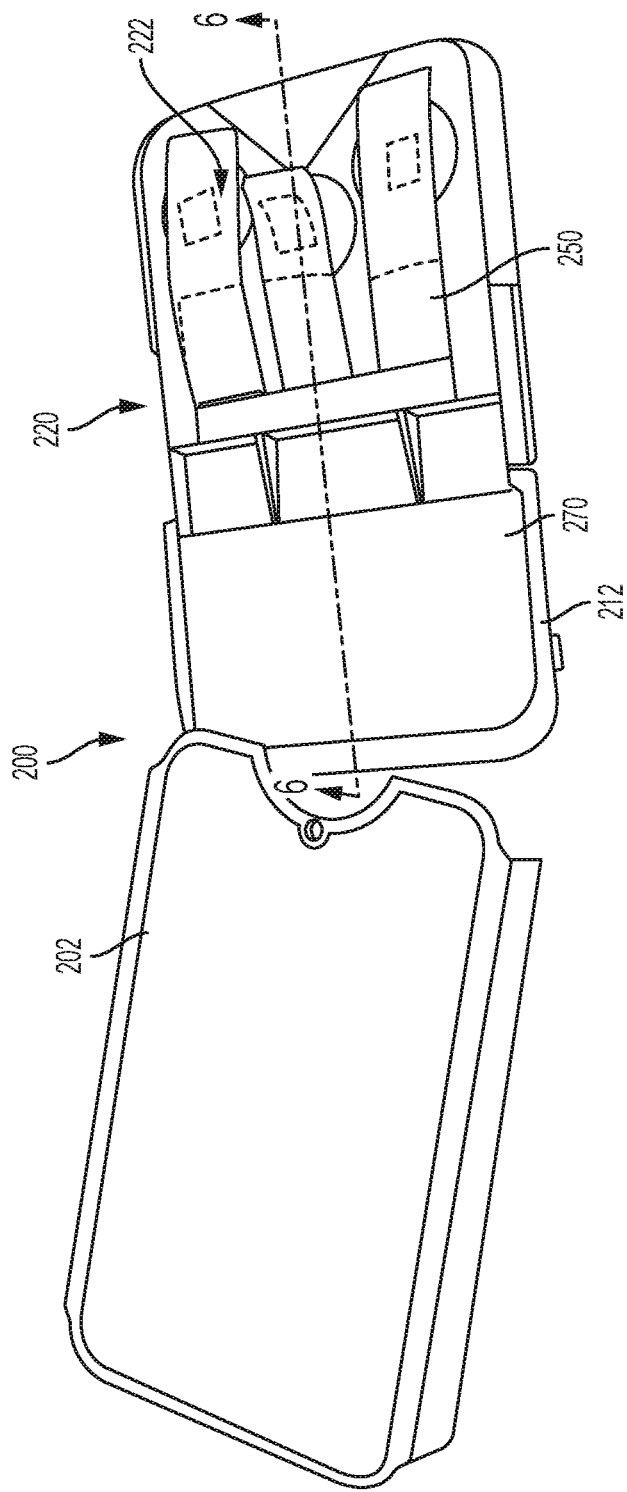
FIG. 2 shows the biological property testing apparatus of FIG. 1 with its cover removed to illustrate interior detail.

FIGS. 1-8C illustrate various components of embodiments of a biological property testing apparatus 200 according to an embodiment of the present disclosure. Referring to FIGS. 1 and 2, a biological property testing apparatus 200 is illustrated. The biological property testing apparatus 200 comprises a cover 202. In FIG. 1, the cover 202 is illustrated in a closed position, and in FIG. 2, the cover 202 is slid to an uncovered position to illustrate internal details of the biological testing apparatus. The cover 202 can have a generally planar surface 204 to enclose components of the biological testing apparatus 200.

Referring again to FIG. 1, exemplary embodiments of the biological property testing apparatus 200 can be generally rectangular and of a compact size to promote portability. In some exemplary embodiments, the biological property testing apparatus 200 can have overall dimensions to correspondingly attach to a mobile device, such as a smartphone. For instance, the biological property testing apparatus 200 can have an overall width 208 between about 100 millimeters and about 180 millimeters, and an overall depth 210 between about 60 millimeters and about 90 millimeters. Such embodiments provide a compact construction and portability to facilitate biological property testing at locations and times convenient to the patient.

Figure 3:
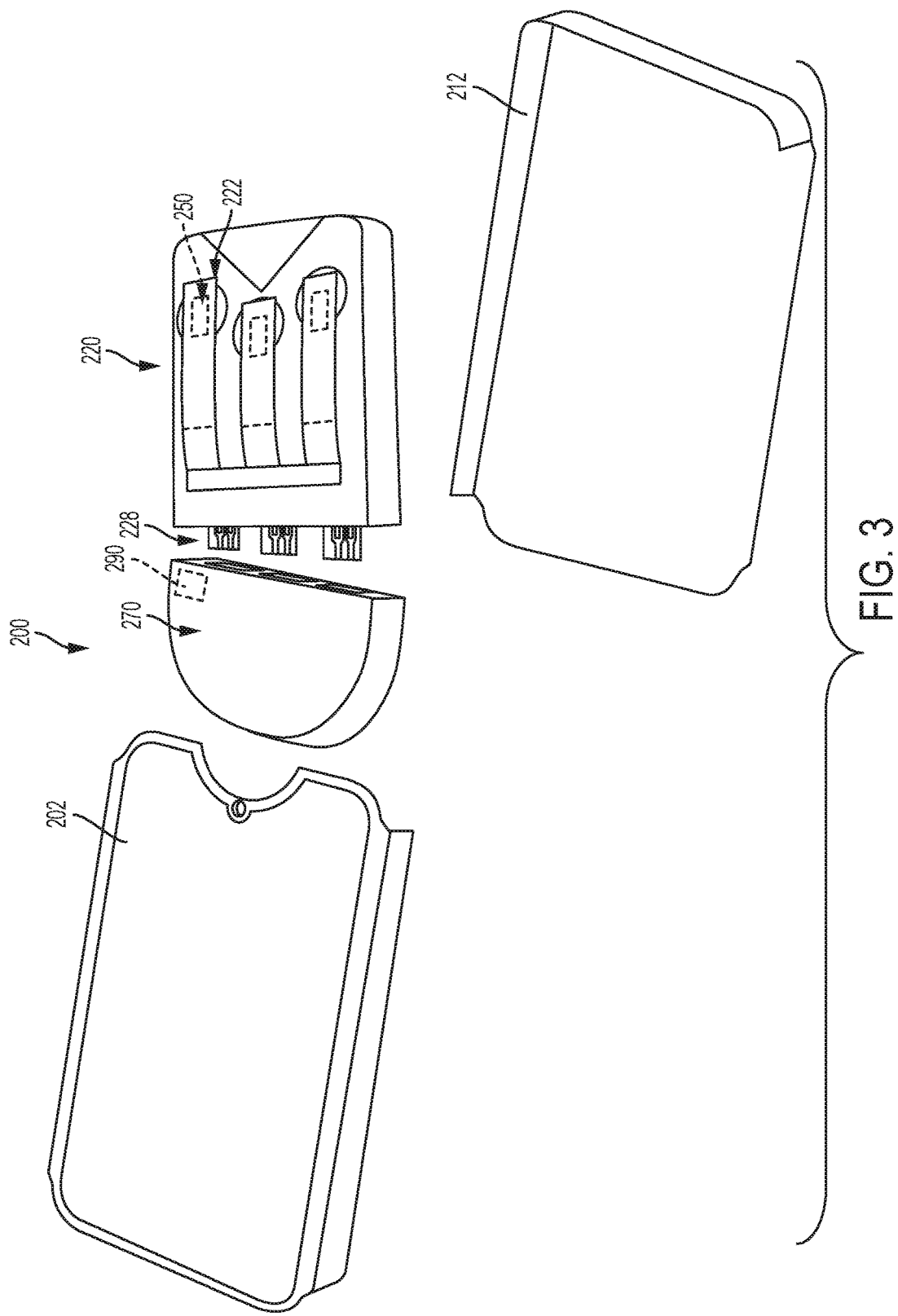
FIG. 3 shows a biological property testing apparatus with a testing module and a meter module disassembled from the housing.

Referring now to FIG. 2, the biological property testing apparatus 200 is illustrated with its cover 202 removed. A housing 212 that can house various components of the biological property testing apparatus 200 is shown. The housing 212 can be shaped and oriented to seat a testing module 220. As is apparent, in some example constructions, the testing module 220 can be removably connected to the housing 212. While FIG. 2 illustrates the testing module 220 connected to the housing 212, FIG. 3 illustrates the testing module 220 removed from the housing 212. For instance, the testing module 220 can be removed by releasing it from the housing 212. Alternatively, the testing module 220 can be slid or lifted from the housing 212. As will be described in further detail below, such embodiments may permit a user to store one or more biological test strips in the testing module 220. When the testing module 220 has been used (discussed elsewhere herein), it can be removed and disposed of and replaced with a new testing module.

Figure 4:
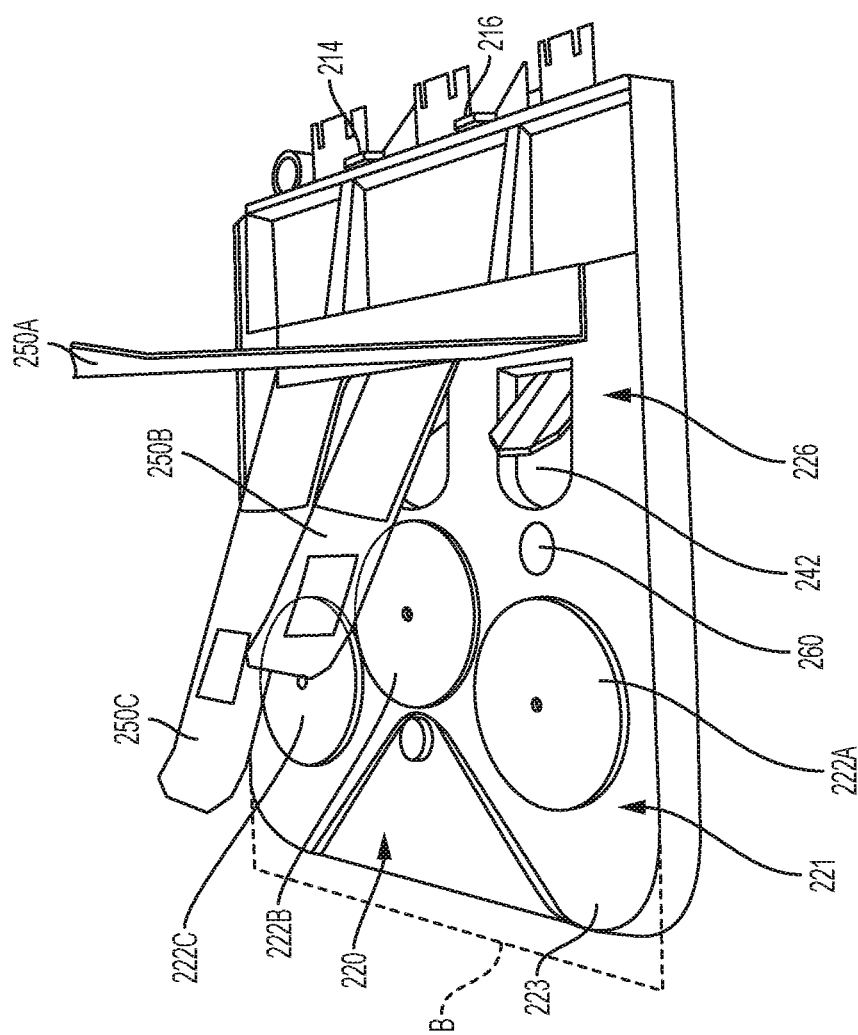
FIG. 4 shows a testing module according to exemplary embodiment.
Figure 5:
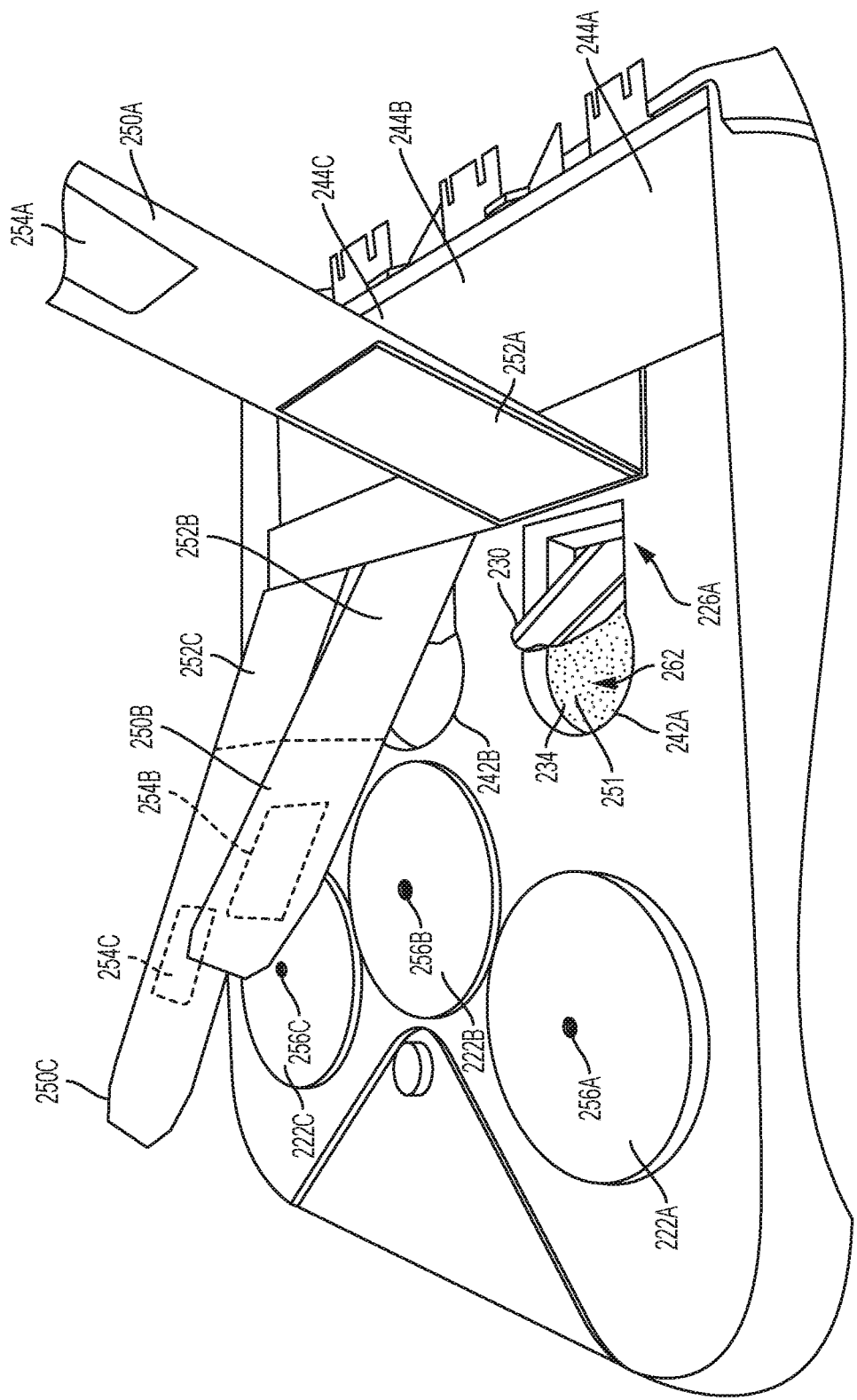
FIG. 5 shows a testing module according to exemplary embodiment.

Referring now to FIG. 4, the testing module 220 can have a base 221 for supporting one or more lancet stations. The base 221 comprises a primary surface 223 extending in a base plane "B". In the example illustrated in FIG. 4, the primary surface 223 can be the top surface, and the base plane "B" can be a plane shown in dotted lines in FIG. 4 that includes the top surface. In certain embodiments, the biological testing device can be positioned on a support surface such as a table top (not shown). In such cases, the base plane can be a horizontal plane parallel to the support surface on which the biological testing device is placed.

As mentioned above, the biological property testing apparatus 200 comprises a plurality of lancet stations supported by the base 221. In the exemplary embodiment of FIGS. 4 and 5, a first lancet station 222A, a second lancet station 222B, and a third lancet station 222C are illustrated. Each of the lancet stations 222A, 222B, and 222C includes a lancet. For example, referring to the cross-sectional view of FIG. 6, a representative lancet station 222 is illustrated, and includes a lancet 224. The lancet 224 can be supported by the lancet station 222 such that it is generally stationary relative to a user's finger, thumb or another portion of the body during lancing.

Each lancet station 222 comprises a lancet station housing 225 recessed from the primary surface 223 of the base 221. The lancet 224 can be supported by the lancet station housing 225. The lancet stations 222 can facilitate generation of biological samples. For instance, the lancet stations 222 can facilitate lancing a user's finger or other body part so as to generate blood so as to measure a biological property therefrom. As will be described further below, one or more test strip channels 226 that may house a biological test strip 228 to measure a biological property from the biological sample generated at the lancet station 222. Lancing is discussed in greater detail elsewhere herein.

Figure 6:
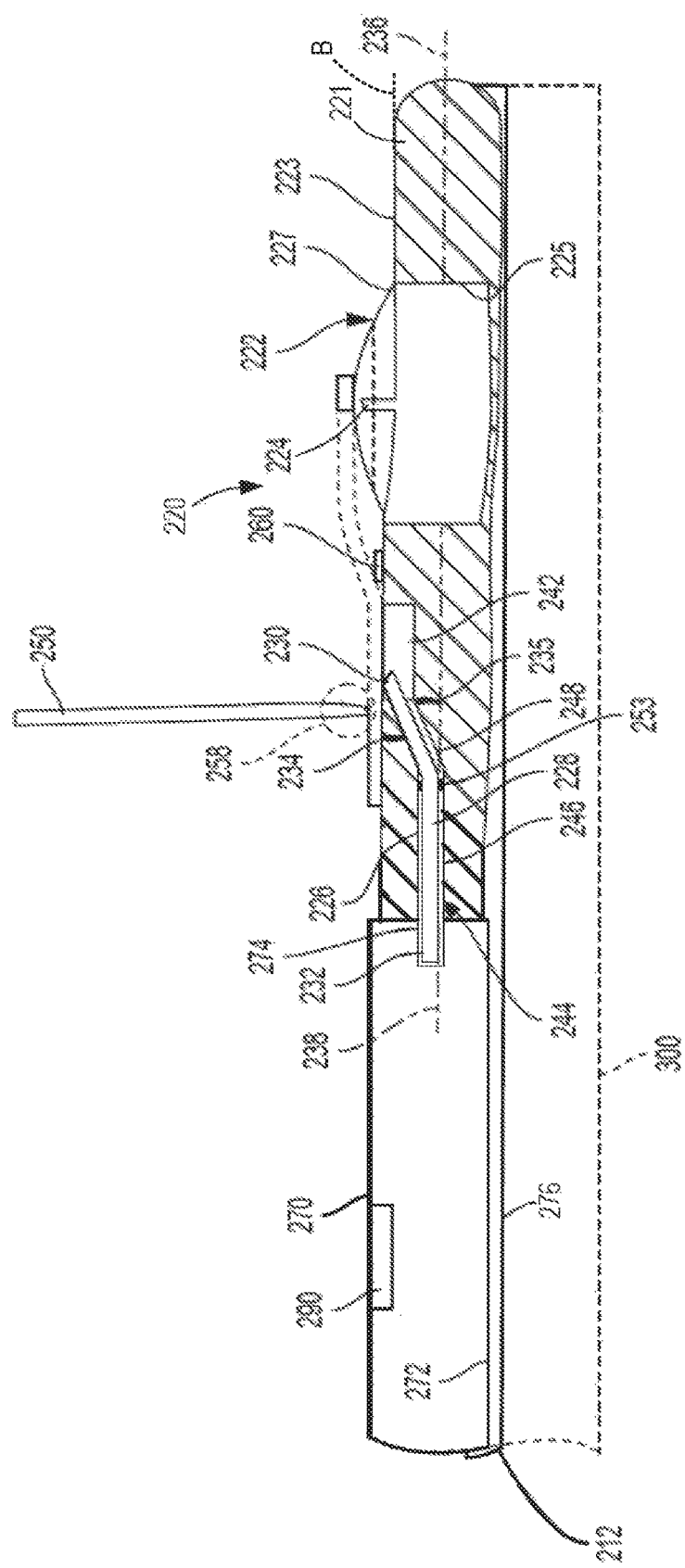
FIG. 6 is a cross-sectional view of the testing module taken along the plane 6-6 shown in FIG. 2.

Continuing with the example embodiment illustrated in FIG. 6, each lancet station 222 includes a lancet cover 227 that is movable between an un-depressed position (shown in solid lines) in which the lancet cover 227 covers the lancet 224 and a depressed position (shown in dotted lines) in which the lancet 224 protrudes through an aperture in the lancet cover 227. In this example, to generate a biological sample, the user would bring their finger, thumb, or another portion of their body toward the lancet cover 227 and apply pressure thereon to move the lancet cover 227 from the un-depressed position to the depressed position. As the lancet cover 227 moves from the un-depressed position to the depressed position, the user's finger, thumb or another portion of the body moves toward the lancet 224, and can be lanced to generate the biological sample. In some embodiments, the lancet cover 227 may return from its depressed position to the un-depressed position when the user stops applying pressure on the lancet cover 227. Advantageously, such embodiments allow a user to apply a suitable magnitude of pressure on the lancet cover 227 to generate a sufficient quantity of sample, while minimizing pain that may otherwise occur if excessive pressure is applied while lancing.

As shown in FIG. 6, according to some exemplary embodiment, the testing module 220 can have a test section 244. In such cases, components of the testing module 220 that are associated with sample generation may be positioned outside of the test section 244, and components of the testing module 220 that are associated with biological property measurement can be part of the test section 244. For instance, referring to FIGS. 5 and 8C, the first test section 244A can include the sample cavity 242A, the first test strip channel 226A having a biological test strip 228. The testing module 220 includes a second test section 244B, having a second sample cavity 242B, and second test strip channel 226B and a third test section 244C, having a third sample cavity 242C and third test strip channel 226C.

While the biological test strip 228 is illustrated as a separate component housed in the test strip channel 226 in FIG. 6, it should be understood that embodiments whereby components of a biological test strip 228, such as chemicals that respond to certain chemicals in a biological sample may be provided integral with the base 221. For instance, the test strip channel can be coated or provided with chemicals present in commercially-available test strips. In such cases, once a user generates a biological sample (e.g., by lancing at a lancet station 222), the sample may be collected by a sample cavity 242, and sent to the test strip channel 226 due to the shape and orientation thereof. In such cases, the biological sample may interact (e.g., coat or wet) the biological test strip 228 or the chemicals (e.g., reactive enzymes) provided in the test strip channels 226, to measure a property change.

In one example, the biological property measured by the biological property testing apparatus 200 can be blood glucose in mg/dL. In this example, the biological sample can be generated by lancing a user's finger or thumb at the lancet station 222. The test strip channel 226 can contain chemicals (e.g., glucose oxidase and/or other components) that may react with glucose in the biological sample. Alternatively, a generally flexible biological test strip 228 can be provided which may include a small spot impregnated with glucose oxidase and/or other components.

Each test strip channel can be aligned with a corresponding lancet station. For instance, the first lancet station 222A can be aligned with the first test strip channel 226A, the second lancet station 222B can be aligned with the second test strip channel 226B, and the third lancet station 222C can be aligned with the third test strip channel 226C. Appreciably, the adjacent positioning of lancet stations 222 and test strip channels 226 provides a compact construction of the testing module 220. For instance, a user may be able to measure a biological property shortly after lancing due to the proximity of the lancet station 222 and the test strip channels 226. Further, such embodiments offer ease of access to biological test strips stored in the test strip channels. Such embodiments can aid in keeping track of which lancet stations and test sections have been used and which have not. It should be understood that, while three sets of lancet stations and test sections are illustrated, any suitable number of sets of lancet stations and test sections (e.g., one, two, four, five, etc.) can be implemented in biological property testing device embodiments.

Figure 7:
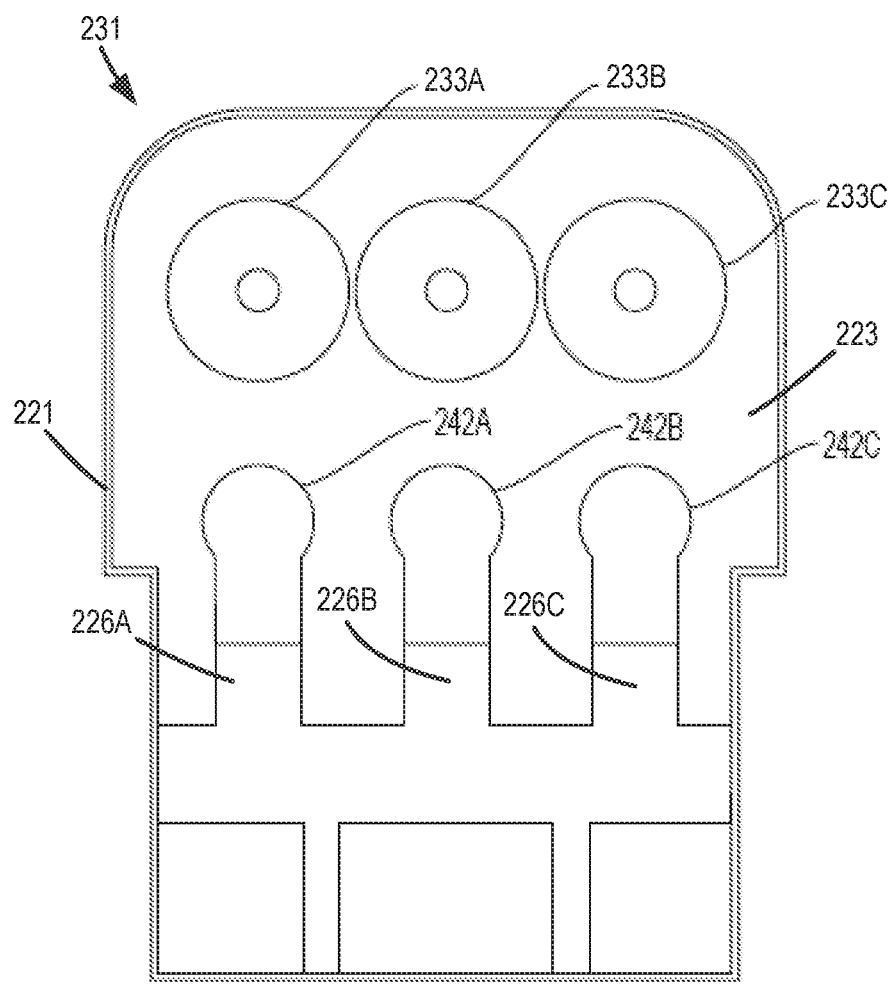
FIG. 7 shows a top view of a biological property testing device carrier according to an exemplary embodiment.

FIG. 7 shows an illustrative biological property testing device carrier 231, which is a testing module without lancet stations or biological test strips. The biological property testing device carrier 231 can include a base 221 with a primary surface 223. The biological property testing device carrier 231 can include one or more lancet station sites 233A, 233B, 233C, each of which may be configured to support a lancet station that includes a lancet. The biological property testing device carrier 231 can include one or more test strip channels 226A, 226B, 226C. Each test strip channel 226A, 226B, 226C may include a main channel portion (246 in FIG. 6) and an angled channel portion (248 in FIG. 6), with the main channel portion and the angled channel portion forming an angle relative to one another. Each test strip channel may be configured to house a biological test strip oriented so that a meter connecting end of the biological test strip is proximate to the main channel portion and a sample end of the biological test strip is proximate to the angled channel portion. As shown, the illustrative biological property testing device carrier 231 includes three lancet station sites 233A, 233B, 233C and three test strip channels 226A, 226B, 226C, with the first lancet station site 233A being aligned with the first test strip channel 226A, the second lancet station site 233B aligned with the second test strip channel 226B, and the third lancet station site 233C aligned with the third test strip channel 226C. When the biological property testing device carrier 231 is assembled into a testing module, a lancet station can be inserted into each lancet station site 233A, 233B, 233C, and a biological test strip can be inserted into each test strip channel 226A, 226B, 226C.

Figure 8A:
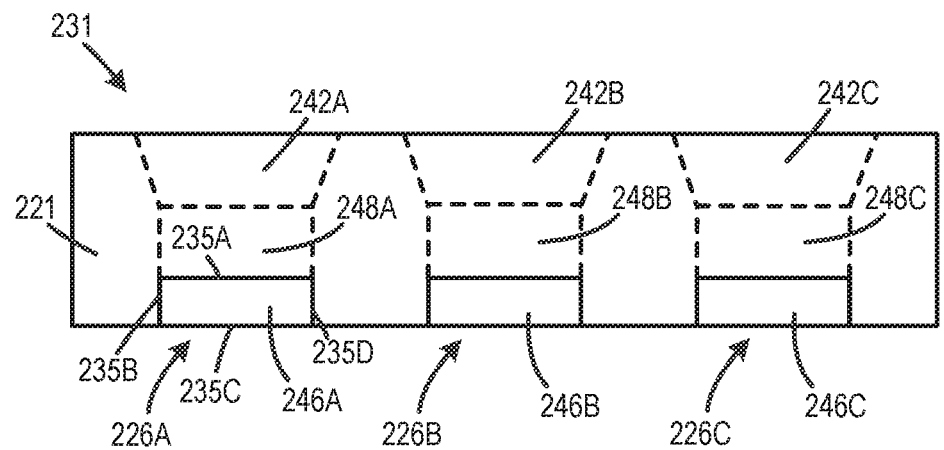
FIG. 8A shows a schematic end view of an illustrative biological property testing device carrier with assembled test strip channels.
Figure 8B:
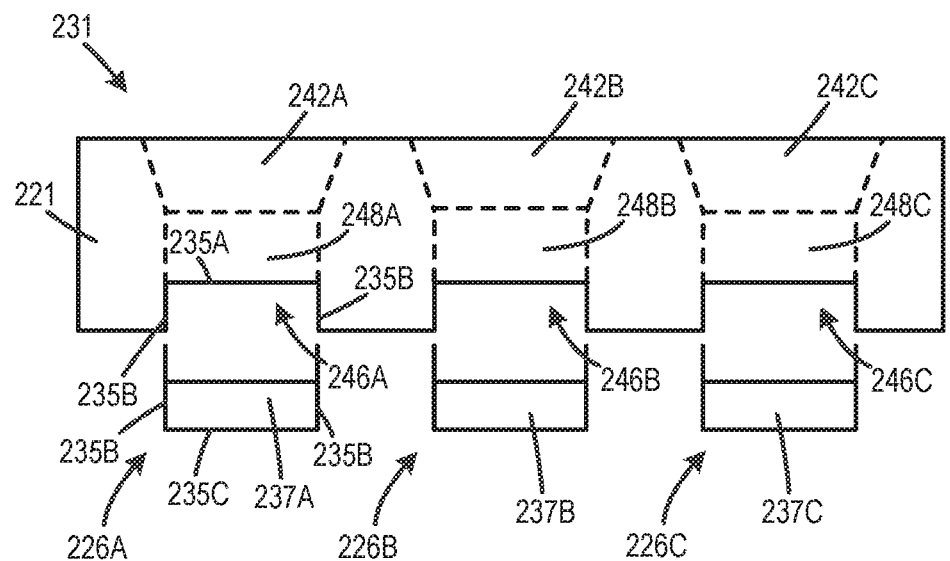
FIG. 8B shows a schematic end view of the illustrative biological property testing device carrier of FIG. 8A with disassembled test strip channels.

FIGS. 8A and 8B show a an illustrative biological property testing device carrier 231 with three test strip channels 226A, 226B, 226C. As shown, each test strip channel 226A, 226B, 226C has a main channel portion 246A, 246B, 246C, an angled channel portion 248A, 248B, 248C, and a sample cavity 242A, 242B, 242C. The test strip channels 226A, 226B, 226C are assembled in FIG. 8A and disassembled in FIG. 8B. Each of the main channel portions 246A, 246B, 246C can be made up of four walls 235 (illustrated in connection with main channel portion 246A). In some embodiments, walls 235A, 235B, 235C can define a rectangular cross section. It should be understood that test strip channels can have a variety of cross sections, such as trapezoidal, elliptical, and so on. As disassembled in FIG. 8B, a removable portion 237A, 237B, 237C is removed from each of the test strip channels 226A, 226B, 226C. At least one of the walls 235A, 235B, 235C that form the test strip channels 226A, 226B, 226C can be integral with the base 221. At least one of the walls 235A, 235B, 235C that form the test strip channels 226A, 226B, 226C can be removable from the base 221. In some embodiments, when a test strip channel is disassembled, positioning a biological test strip in the test strip channel can be significantly easier.

Referring back to FIG. 6, the test strip channels 226 are positioned and oriented to permit ease of access to the biological test strip 228. In some examples, each biological test strip 228 can have a sample end 230 positioned proximate to the lancet station 222 whereby a biological sample is generated. Further, each biological test strip 228 has a meter connecting end 232 proximate to a meter module 270. Each test strip channel 226 can be configured to orient the sample end 230 at an angle 234 of between about 5 degrees and about 90 degrees relative to the primary surface 223 of the base 221, as will be described below. Once oriented as such, the sample end 230 may protrude out of the test strip channel and be in close proximity to the lancet station 222 so that the user may not have to move his/her lanced finger much and quickly measure a biological property.

Continuing with the exemplary embodiment of FIG. 6, internal details of an exemplary test strip channel 226 is illustrated. The test strip channel 226 can be elongate in shape and disposed about a channel axis 238 parallel to the testing module axis 236. Further, the test strip channel 226 can terminate in the sample cavity 242 proximate to the sample end 230 of the biological test strip 228. As mentioned earlier, the sample end 230 of the biological test strip 228 can protrude out of the sample cavity 242 at an angle suitable for ease of access after lancing.

Referring again to the structural features of a representative test strip channel 226 illustrated in FIG. 6, each test strip channel includes a main channel portion 246 and an angled channel portion 248. In the illustrated embodiments, the test strip channel 226 can orient a biological test strip 228 such that the meter connecting end 232 can be proximate to the main channel portion 246 and the sample end 230 can be proximate to the angled channel portion 248. For instance, the meter connecting end 232 can extend out of the main channel portion 246 and the sample end 230 can extend out of the angled channel portion 248. The main channel portion 246 can be generally parallel to the primary surface 223 of the base 221 that extends in base plane B. Further, as seen in FIG. 6, the angled channel portion 248 can form an angle with the main channel portion 246 that equals the angle 234 formed by the sample end 230 of the biological test strip 228. Appreciably, the angle between the angled portion and the testing module axis 236 can also equal between about 5 degrees and about 90 degrees. In the illustrated embodiment, the angled channel portion 248 forms an angle of between about 5 degrees and about 90 degrees with the main channel portion 246. In some embodiments, the angle formed by the main channel portion 246 and the angled channel portion 248 can be between 5 degrees and 45 degrees. Angles can be selected based on the depth of the sample cavity, the diameter of the sample cavity, the length of the biological test strip, and a variety of other factors.

Figure 8C:
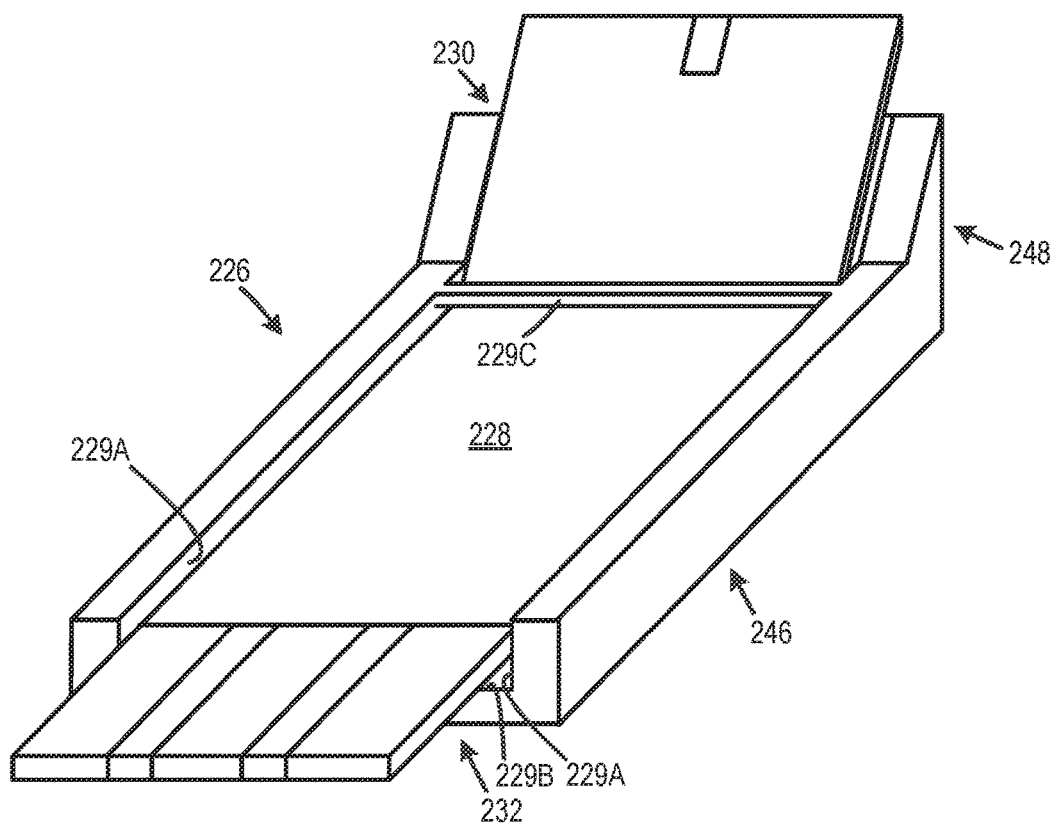
FIG. 8C shows a test strip channel according to an exemplary embodiment.

FIG. 8C illustrates an example test strip channel 226. The test strip channel 226 can include a main channel portion 246 and an angled channel portion 248. A biological test strip 228 can be housed in the test strip channel 226. As shown, the biological test strip 228 can be oriented so that a meter connecting end 232 is proximate to the main channel portion 246 and a sample end 230 is proximate to the angled channel portion. The test strip channel 226 can include a side walls 229A, a base wall 229B, and a bar 229C. The bar 229C can be connected to the side walls 229A proximate to where the angled channel portion 248 forms an angle with the main channel portion 246. In this way, the bar 229C can be configured to conform the biological test strip 228 housed in the test strip channel 226 to the angle formed by the main channel portion 246 and the angled channel portion 248.

In certain exemplary embodiments, the biological test strip 228 positioned in the test strip channel may generally follow the contours of the test strip channel. In such examples, the biological test strip 228 can be generally flexible relative to the base 221. For instance, the meter connecting end 232 of the biological test strip 228 protrudes out of the main channel portion 246, and can be generally parallel to the primary surface 223 of the 226 base 221 (and in turn, to the testing module axis 236 of the testing module 220). Further, the biological test strip 228 can be angled to match the angle of the angled portion of the testing channel. Accordingly, the sample end 230 of the biological test strip 228 protrudes out of the angled portion, and can be oriented at an angle of about 5 degrees and about 90 degrees with respect to the primary surface 223 (and in turn, the testing module axis 236, as well as the meter connecting end 232). Such embodiments permit housing 212 and orienting a biological test strip 228 to facilitate ease of measuring a biological property. The user can more readily access the sample end 230 because of the angled orientation, than, for instance, if the sample end 230 were flush with the primary surface 223 of the base 221 (or were parallel thereto).

Continuing with the exemplary embodiment illustrated in FIG. 6, the test strip channels 226 can be of a "universal size" with dimensions sufficient to house biological test strips having a wide range of sizes. Commercially available biological test strips can be generally rectangular in shape having a length of between about 25 millimeters and about 35 millimeters, and width of between about 4 millimeters and about 7 millimeters. The test strip channels 226 can be sized to accommodate such commercially available biological test strips. For instance, in some examples, the main channel portion 246 of the test strip channel 226 has a length of between about 15 millimeters and about 24 millimeters, and the angled channel portion 248 of the test strip channel 226 has a length of between about 4 millimeters and about 7 millimeters. The main channel portion 246 and the angled channel portion 248 of the test strip channel have a common width of between about 5 millimeters and about 9 millimeters. More generally, in some exemplary embodiments, each test strip channel 226 can have a length that is between about 55% and about 700, of the length of the biological test strip 228, and generally have a width approximately equal to the width of the biological test strip 228.

Referring again to FIG. 6, exemplary embodiments can include components for sealing certain portions of the testing module 220 prior to use. In some examples, the biological property testing apparatus 200 comprises a cover tab 250 coupled to the base 221 and movable from a covered position to an uncovered position (e.g., using a hinged connection). With reference to FIG. 4, all three cover tabs 250A, 250B, 250C are shown in the uncovered position. The cover tabs can be configured to cover and uncover the lancet stations, an alcohol swab section, the test section, and other suitable components of the testing module.

Referring back to FIGS. 4 and 5, each cover tab 250 can have a corresponding moisture barrier that can seal off a corresponding sample cavity 242. For instance, a first moisture barrier 252A can seal off the first sample cavity 242A when the first cover tab 250A is in the covered position, while the first moisture barrier 252A may not seal off the first sample cavity 242A when the first cover tab 250A is in the uncovered position. Similarly, a second moisture barrier 252B can be coupled to the second cover tab 250B for sealing off the second sample cavity 242B when the second cover tab 250B is in its covered position. The second moisture barrier 252B may not seal off the second sample cavity 242B when the second cover tab 250B is in its uncovered position. Further, a third moisture barrier 252C can be coupled to the third cover tab 250C for sealing off the third sample cavity 242C (best seen in FIG. 8A) when the third cover tab 250C is in its covered position. The third moisture barrier 252C may not seal off the third sample cavity 242C when the third cover tab 250C is in its uncovered position The moisture barriers permit maintaining areas surrounding test strip channel 226 to be flushed with dry nitrogen prior to sealing with the cover tab 250. The flexible cover tab 250 provides a secondary cover to the lancet cover 227. Further, in some embodiments, a sealant 253 can be provided in a main channel portion 246 of the test strip channel. The sealant 253 can further reduce, or prevent moisture from reaching the sample cavity 242 through the main channel portion 246. Appreciably, such embodiments can reduce moisture intrusion into the sample cavity 242 and/or the biological test strips thereby providing for a sterile testing module 220.

Referring again to FIG. 5, the cover tab can include a sterile barrier for sealing off the lancet apertures. For instance, a first sterile barrier 254A can be coupled to the first cover tab 250A for sealing off the first lancet aperture 256A when the first cover tab 250A is in the covered position. The first sterile barrier 254A may not seal off the first lancet aperture 256A when the first cover tab 250A is in the uncovered position. Similarly, a second sterile barrier 254B coupled to the second cover tab 250B for sealing off the second lancet aperture 256B when the second cover tab 250B is in its covered position. The second sterile barrier 254B may not seal off the second lancet aperture 256B when the second cover tab 250B is in its uncovered position. Further, a third sterile barrier 254C can be coupled to the third cover tab 250 for sealing off the third lancet aperture 256C when the third cover tab 250 is in its covered position.

The third sterile barrier 254C may not seal off the third lancet aperture 256C when the third cover tab 250 is in its uncovered position.

As indicated previously, in some exemplary embodiments best illustrated in FIG. 6, a hinge 258 facilitates movement of the cover tab 250 between its covered and uncovered position. The cover tab 250 can be further movable (e.g., using the hinge 258) to a re-covered position in which the cover tab 250 covers the sample cavity 242 and the lancet 224 aperture after use. Such a re-covered position can reduce the incidence of inadvertent lancing and of accidentally contacting the tested biological sample. Optionally, each of the test sections can include desiccant 251 (e.g., silica gel) in a corresponding sample cavity 242 to reduce negative effects of moisture intrusion into the sample cavity 242. Such embodiments provide a sterile testing module 220 that reduces moisture intrusion, as well as keep the testing module 220 clean and free of microorganisms. Such embodiments improve accuracy of test results as a result of sterile and moisture-tight packaging of the testing module 220.

Further, some example embodiments can provide users with the ability to sterilize their finger, thumb or another portion of their body prior to testing. In one example, shown in FIG. 4, the base 221 includes an alcohol swab section 260 that may support one or more alcohol swabs. In such cases, the cover tab 250 can cover 202 the alcohol swab section 260 when in the covered position and may not cover 202 the alcohol swab section 260 when in the uncovered position. Such examples facilitate improving accuracy of test results and reducing the risk of infection.

Referring back to FIG. 3, the biological property testing apparatus 200 according to some examples can include a meter module 270 removably attachable to one side (e.g., first side 272) of the housing 212. For instance, the meter module 270 may removably attach (e.g., by a snap fit, or using fasteners) to the testing module 220 adjacent to the meter connecting end 232 of the biological test strips. The meter module 270 can include measuring equipment to facilitate measurement of a biological property, as discussed with reference to the embodiments illustrated in FIGS. 9-16 below. Referring back to FIG. 6, the meter module 270 can include an input port 274 for receiving the meter connecting end 232 of the biological test strip 228 when the testing module 220 and the meter module 270 are attached to the housing 212. The other side (e.g., second side 276 opposite to the first side 272) of the housing 212 can include adhesive to adhere the housing 212 to a mobile device 300 (shown in phantom). In the orientation illustrated in FIG. 6, the first side 272 is the top side of the housing 212, while the second side 276 is the bottom side of the housing 212.

With continued reference to FIG. 6, some example embodiments may permit transmitting the results of a biological property measurement completed by the biological property testing apparatus 200. For instance, in the example illustrated in FIG. 6, the meter module 270 includes a wireless transmitter 290 to communicate a biological property test result to a mobile device 300. In some examples, the wireless transmitter 290 can be a Bluetooth compatible device that can send test results to the mobile device 300 using Bluetooth communication protocol. Alternatively, other wireless protocols for transmitting test results (e.g., WiFi, 4G, and the like) can be used to send the test results to the mobile device 300. Advantageously, such devices permit the user to initiate a test, and/or record, monitor and communicate (e.g., with a healthcare provider) test results as discussed elsewhere herein with reference to FIGS. 17A and 17B.

Figure 9:
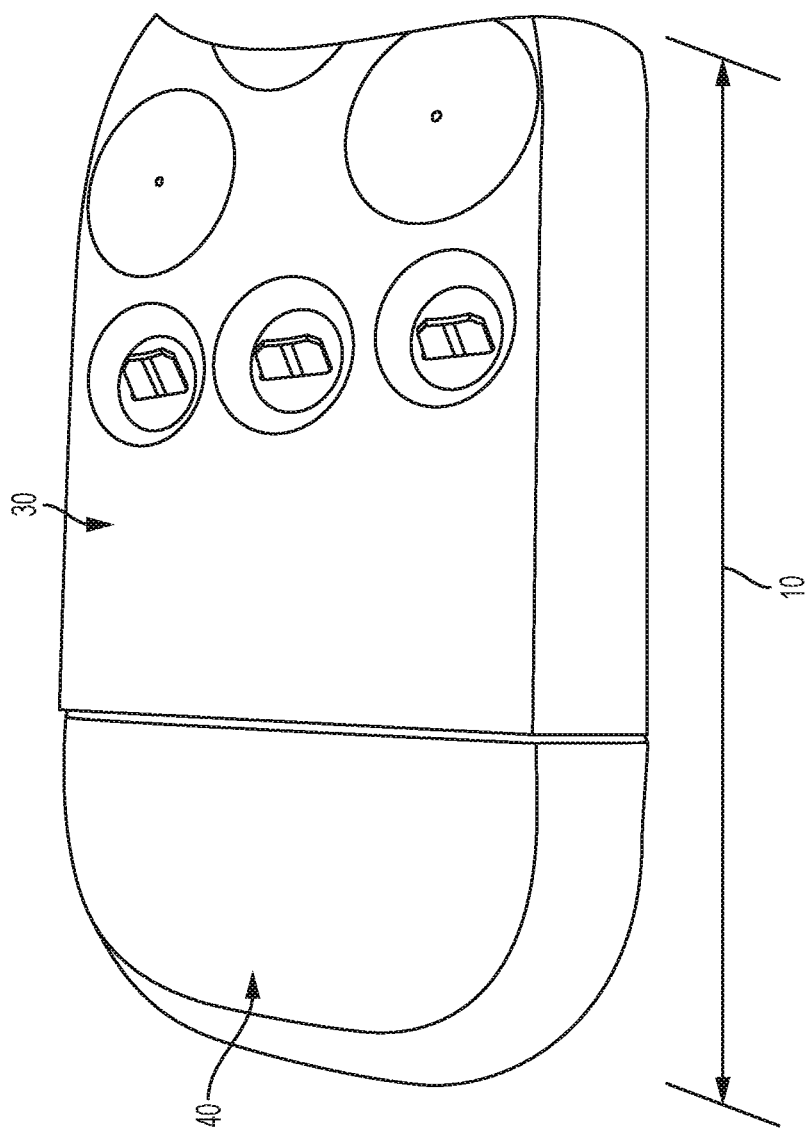
FIG. 9 shows an illustrative biological property testing device for attaching to the back of a mobile device.
Figure 10:
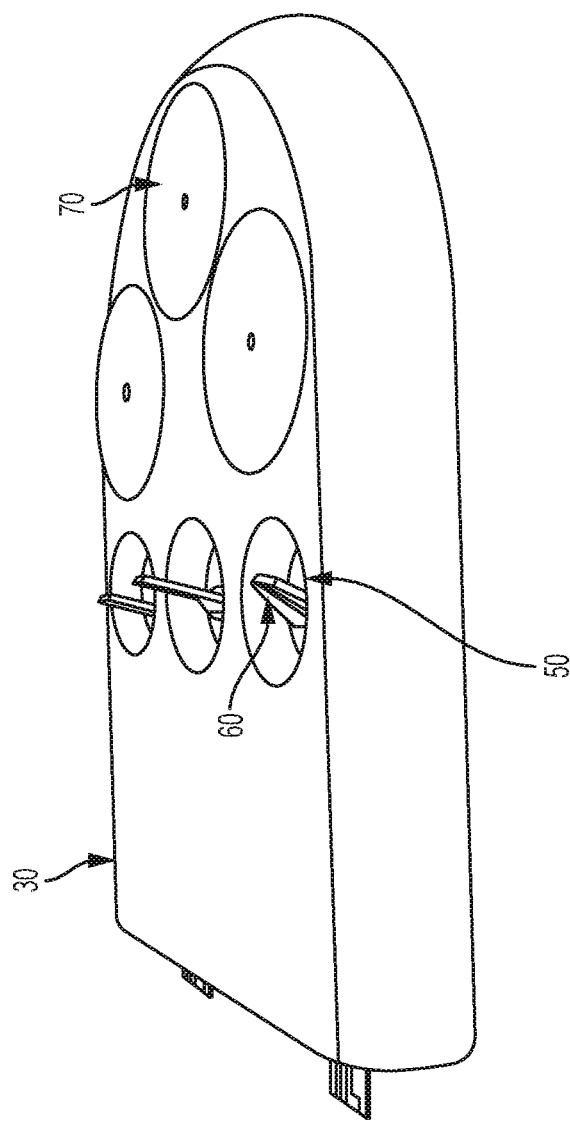
FIG. 10 shows the testing module portion of the biological property testing device of FIG. 9.
Figure 11:
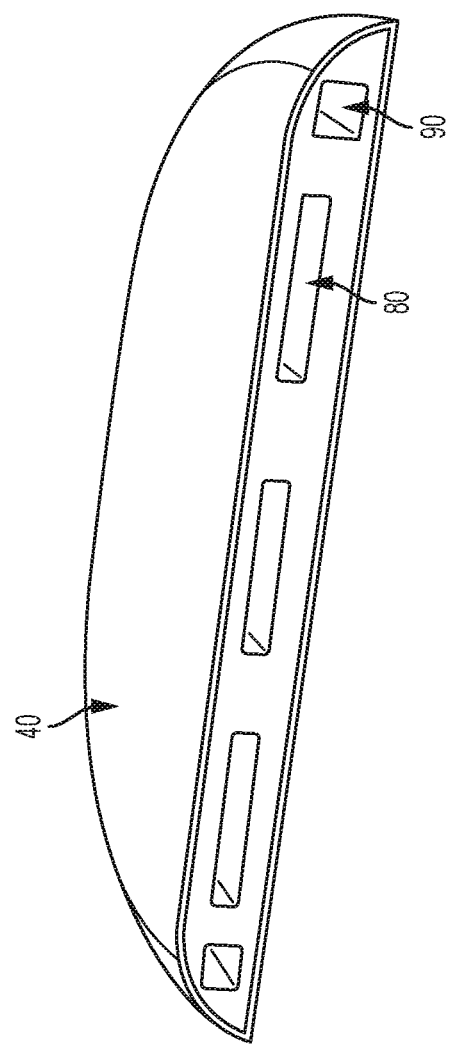
FIG. 11 shows the meter module portion of the biological property testing device of FIG. 9.

As shown in FIGS. 9-11, embodiments can include a biological property testing device 10 according to another embodiment. The embodiment illustrated in FIGS. 9-11 share many similarities with the embodiment illustrated in FIGS. 1-8C. In many cases, the biological property testing device 10 can be removably attached to a mobile device. The biological property testing device 10 can include a testing module 30 and a meter module 40. The testing module 30 can include one or more test strip stations 50. Each test strip station 50 can be surrounded by a cavity or well and can include a biological strip 60. Biological strips 60 can be stabilized at an angle (e.g., 5-90°) to testing module 30 (see FIG. 9). The preferred angle of biological strips 60 to testing module 30 can be about 90 degrees, though angles below or slightly above 90 degrees are contemplated. In some embodiments, testing module 30 can include one or more lancet stations 70. Each lancet station 70 can be built into testing module 30 or removably inserted into testing module 30. Each lancet station 70 can include an enclosed lancet. The meter module 40 may have measuring equipment configured to measure a property of a biological sample (e.g., a blood sample). The meter module 40 can include one or more meter sockets 80 that can each receive a biological strip 60.

Figure 12:
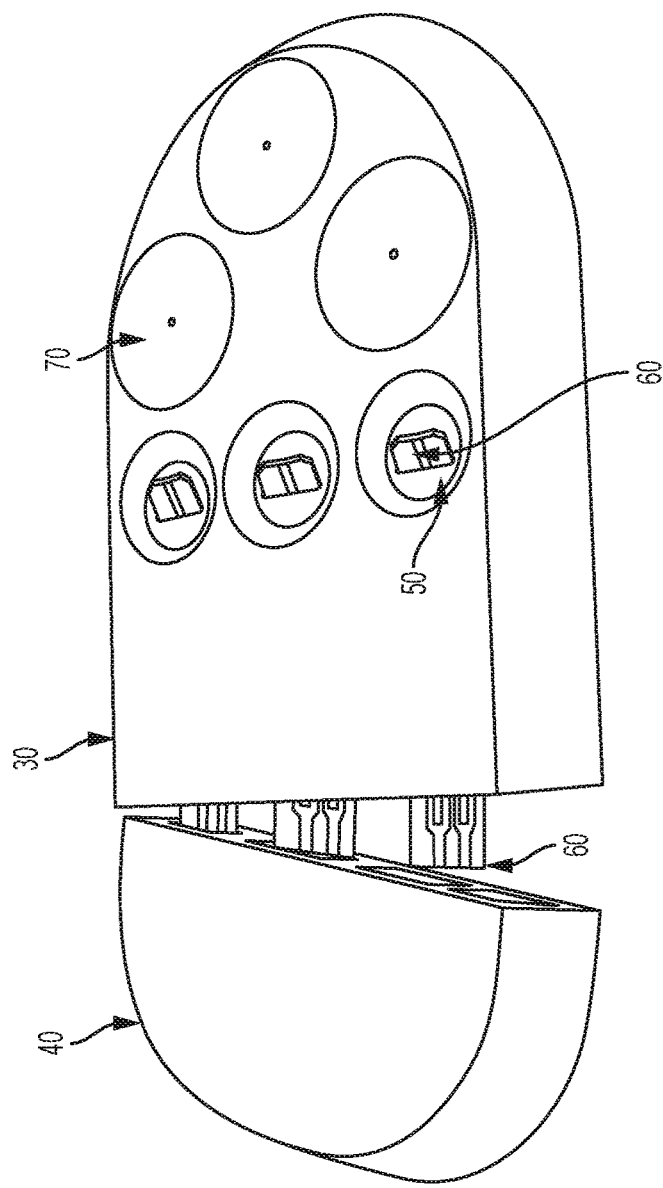
FIG. 12 shows the biological property testing device of FIG. 9 with the testing module of FIG. 10 detaching from the meter module of FIG. 11.
Figure 13:
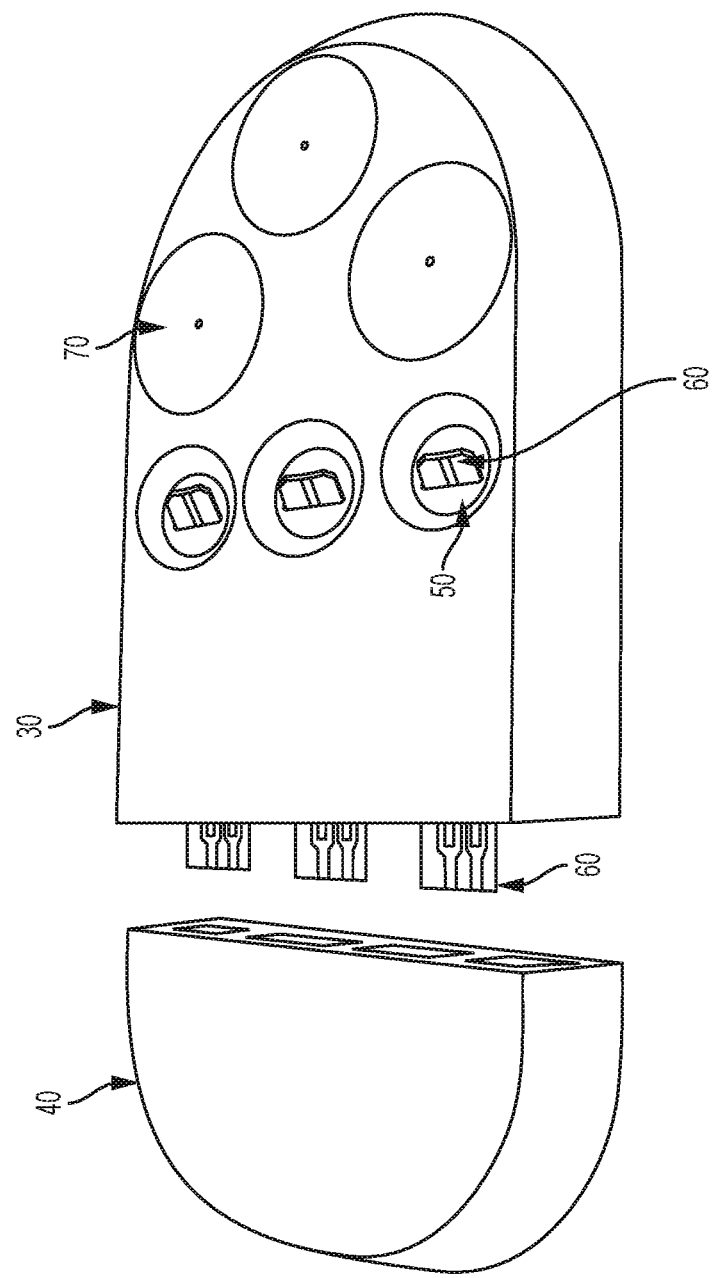
FIG. 13 shows the biological property testing device of FIG. 9, with the testing module of FIG. 10 fully detached from the meter module of FIG. 11.

The testing module 30 can be connectable to the meter module 40. The meter module 40 can include guide pins or a guide socket 90 to assist in proper alignment of the testing module 30 to the meter module 40. When the testing module 30 can be attached to meter module 40, any biological strips 60 contained within the test strip stations 50 are coupled with meter module 40 through meter sockets 80 to enable communication. When the test strip stations 50 and any lancet stations 70 of the testing module 30 have been used, the testing module 30 can be decoupled from the meter module 40, and a new testing module can be coupled to the meter module 40. FIG. 12 shows the testing module 30 being partially decoupled from the meter module 40, and FIG. 13 shows the testing module 30 and meter module 40 as completely decoupled. The biological property testing device is described in greater detail in U.S. Pat. No. 9,237,866, which is titled "Blood Glucose Management" and co-owned with the present application, and which is hereby incorporated by reference herein in its entirety. U.S. Pat. No. 8,647,357, which is titled "Lancet Device with Flexible Cover" and is likewise co-owned with the present application, also provides additional detail on the biological property testing device and is also hereby incorporated by reference herein in its entirety.

Figure 14:
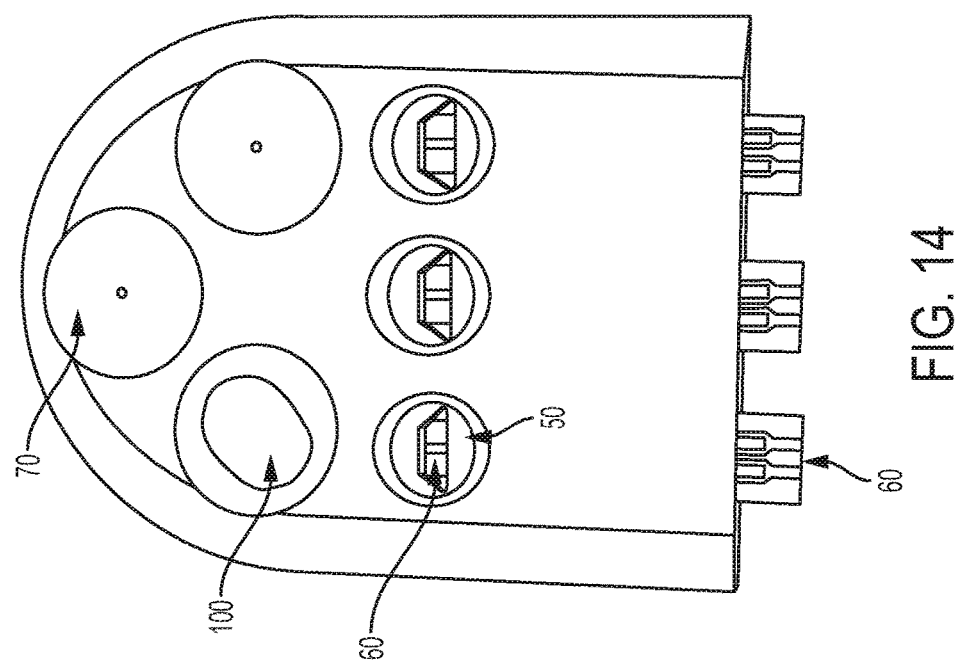
FIG. 14 shows the testing module of FIG. 10, with a sterile barrier over one lancet station.
Figure 15:
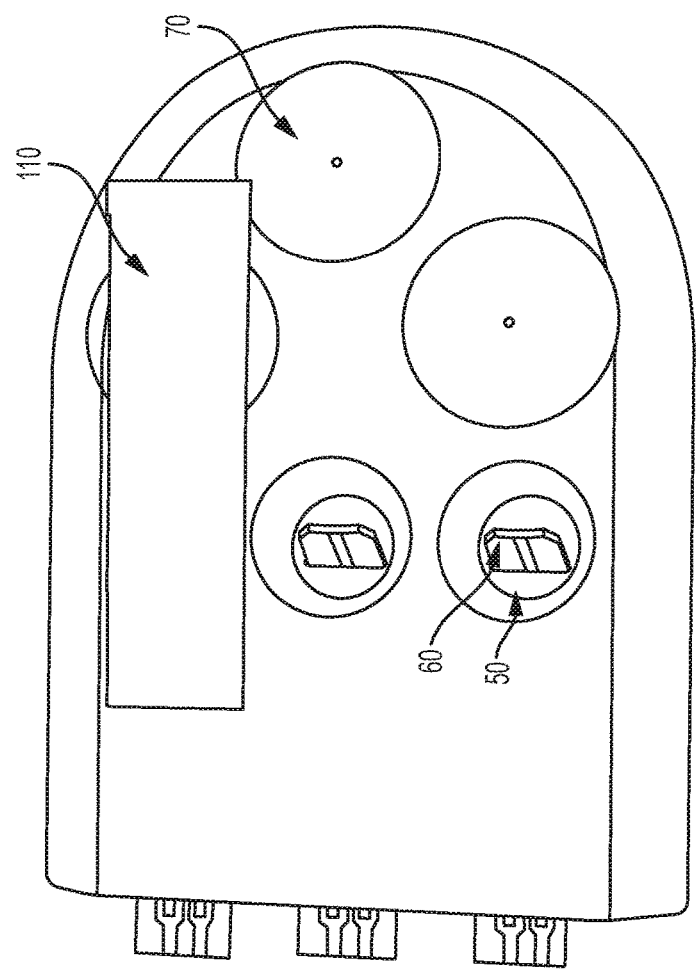
FIG. 15 shows the testing module of FIG. 14, with a removable cover over a lancet station and a test strip station.
Figure 16:
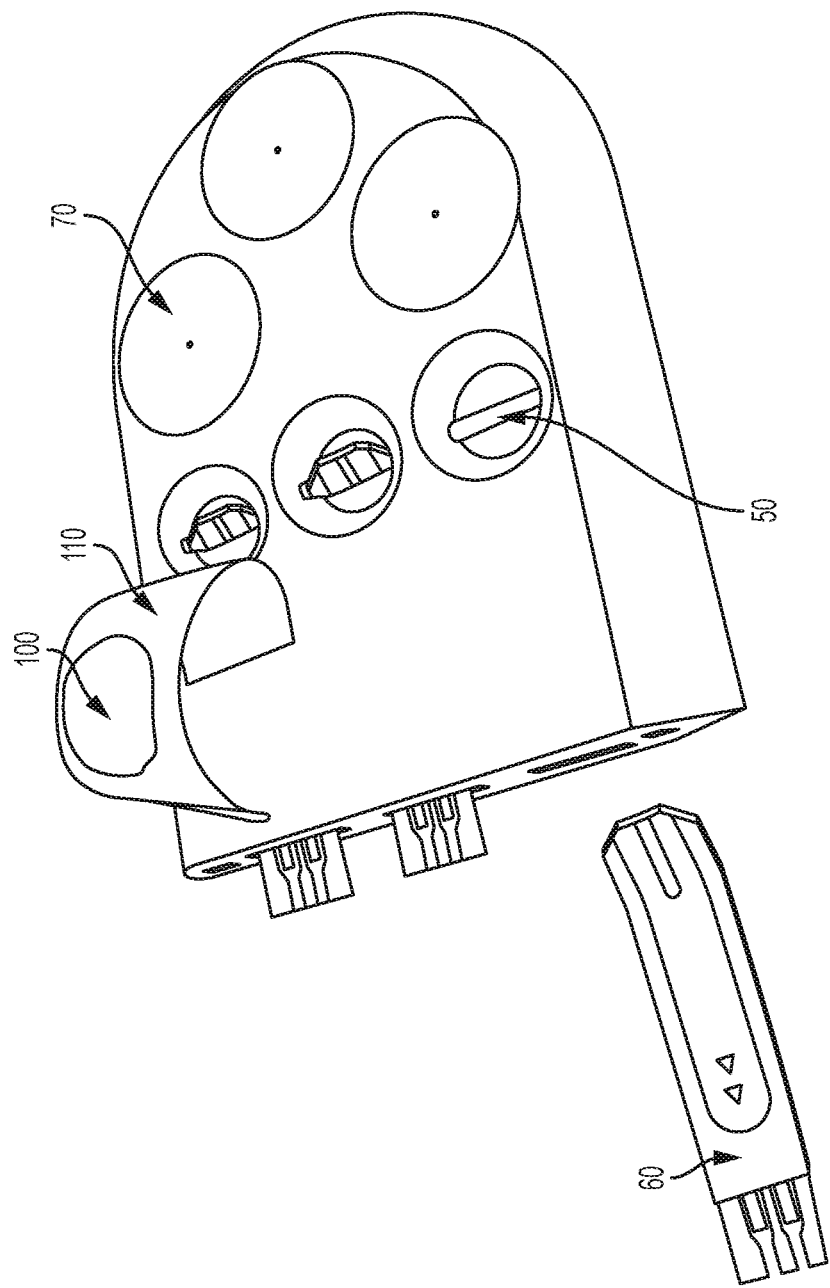
FIG. 16 shows the testing module and cover of FIG. 15, with the cover opened to reveal a lancet station with the sterile barrier of FIG. 14 removed and a test strip station.

As shown in FIG. 14, in some embodiments, the lancet station 70 can be covered by a sterile barrier 100. In some embodiments, the lancet station 70, sterile barrier 100, and test strip station 50 can themselves be covered by a flexible cover 110, shown in FIGS. 15-16. The flexible cover 110 can be peeled off of lancet station 70 and test strip station 50, thereby removing sterile barrier 100 from lancet station 70. The flexible cover 110 can be attached hingedly to testing module (e.g., via a die cut area). The flexible cover 110 provides a moisture barrier to the test strip station 50, allowing the cavity or well surrounding test strip station 50 to be flushed with dry nitrogen prior to sealing with the flexible cover 110. The flexible cover 110 provides a secondary cover to the lancet station 70 and sterile barrier 100.

Referring again to FIGS. 15-16, when biological strip 60 can be coupled to meter module 40, the measuring equipment of meter module 40 can determine a blood glucose measurement (or other biological sample measurement). In certain embodiments, the meter module 40 can transmit a signal representative of the blood glucose measurement to the mobile device (or to a separate device) for display. The meter module 40 can include a wireless transmitter (e.g., a Bluetooth transmitter) that can be configured to communicate with components in the mobile device (or other device). The meter module 40 can provide a wired connection to other devices. Again, additional detail on use of the biological property testing device 10 can be found in the above-referenced U.S. Pat. No. 9,237,866 and U.S. Pat. No. 8,647,357.

Figure 17A:
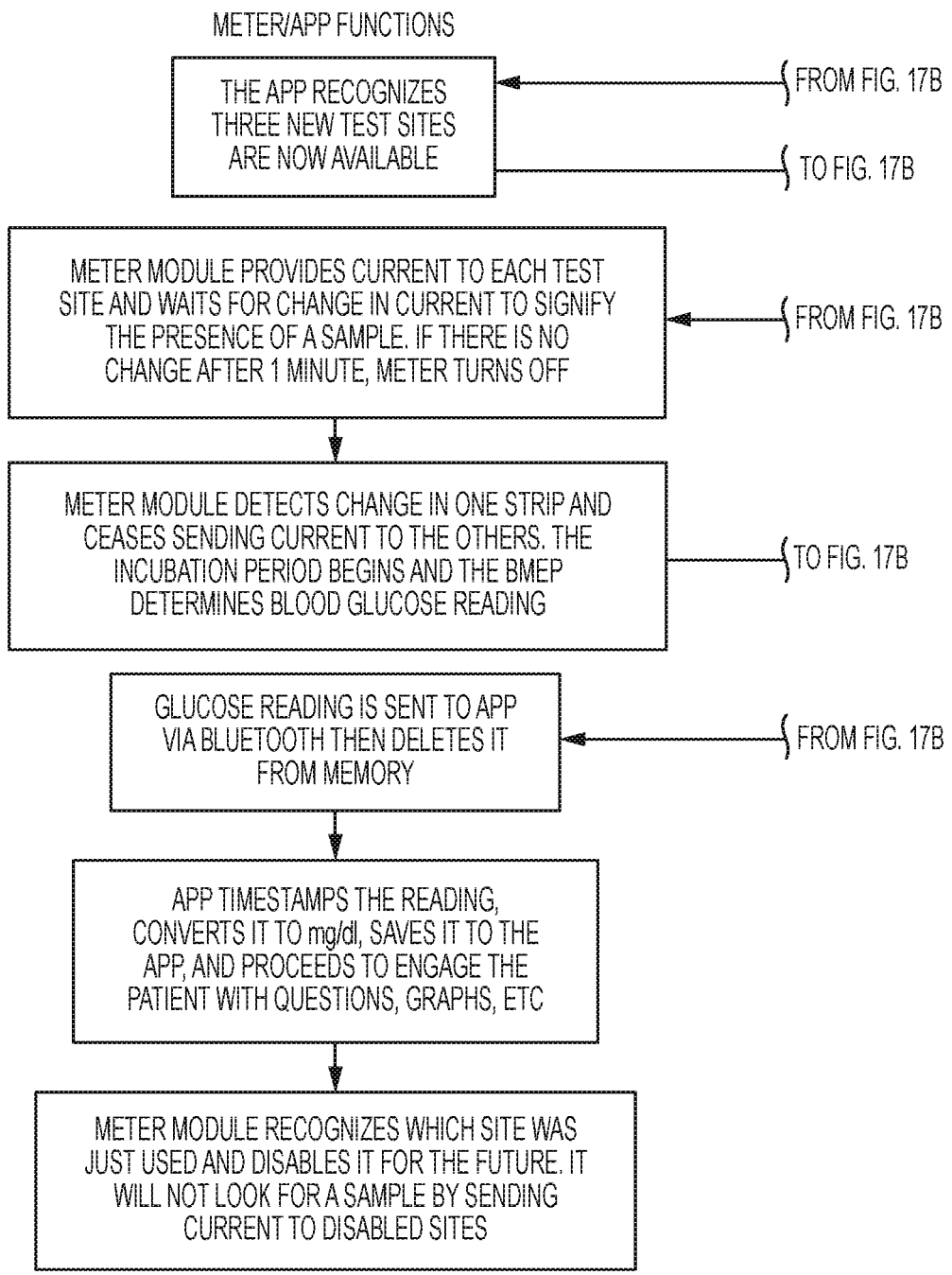
FIGS. 17A and 17B illustrate a flow chart showing a portion of the functions of the meter module, mobile application, and user in accordance with embodiments of the present disclosure.
Figure 17B:
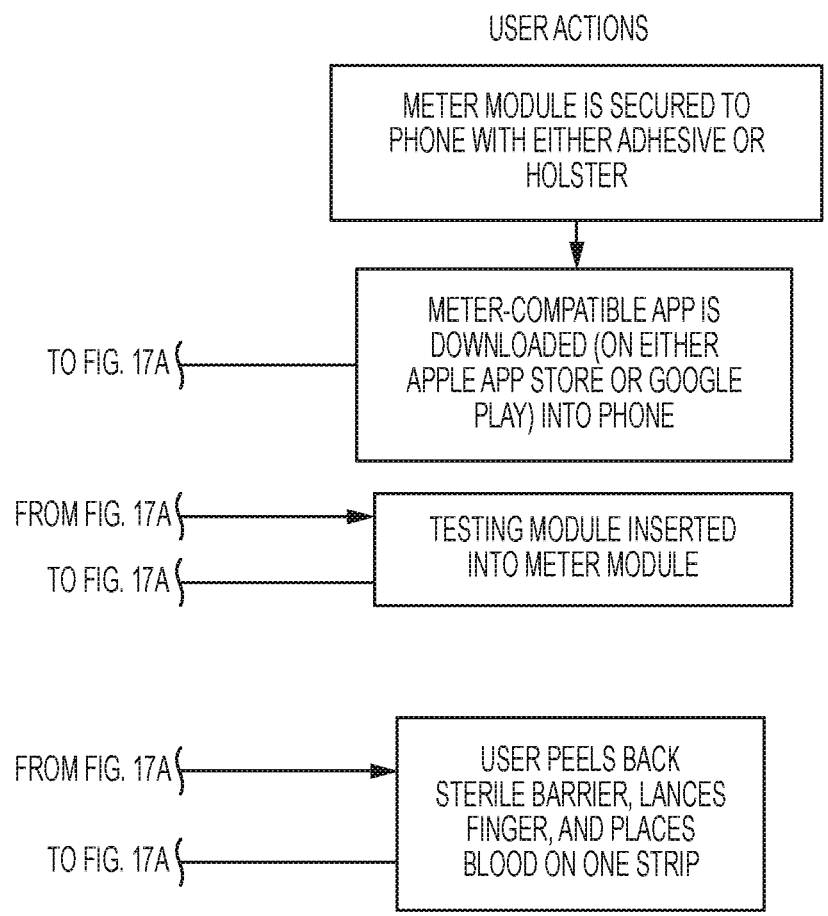

Referring to FIG. 17A-17B, a user of the biological property testing device 10 can use an application of mobile device to ready the meter module 40 for testing. Upon a user telling the mobile device application that he/she is connecting a new testing module 30 to the meter module 40, the mobile device application sends a signal to the meter module 40. Upon receiving the signal, the meter module 40 recognizes the new available test sites and provides current to each test site. Upon a user opening the mobile device application where an existing testing module 30 can be connected to meter module 40, the meter module 40 and the mobile application confirm which test sites are available for use, if any. If no sites are available for use, the meter module 40 signals to the mobile device application that a new testing module 30 may be needed and the mobile device application communicates the information to the user.

If any sites are available for use, whether in a newly attached testing module 30 or a previously used testing module 30, the meter module 40 waits for a change in current caused by blood on one of the biological strips 60. If no change in current is detected after one minute, meter module 40 turns off the current. After the user lances his/her finger with a lancet station 70 or a separate lancet and applies blood to one of the biological strips 60, the meter module 40 will detect a change in current. Upon detecting this change, the meter module 40 will cease providing current to the other strips, calculate a reading from the biological strip, and send the reading and location of the used test site to the mobile device application. The meter module 40 will store the location of the used test site in its own memory and will refrain from sending current to the used test site in the future. After confirmation that the mobile device application received the data, the meter module 40 turns off. The mobile device application timestamps the blood glucose reading and converts it to mg/dL, and saves it to the mobile device. The mobile device application is described further and in greater detail in U.S. patent application Ser. Nos. 15/149,119, 15/149,120, 15/149,121, which are each titled "Blood Glucose Management" and co-owned with the present application, and which are hereby incorporated by reference herein in their entirety.

Embodiments of the present disclosure provide one or more advantages. Biological property testing devices according to some embodiments can provide ease of use and compact construction, because of adjacent location of lancet stations and test strip channels. Further, the orientation of the test strip channels provides ease of access to the biological test strips stored therein. Biological property testing devices according to certain embodiments of the present disclosure provide sterile packaging to improve test results and reduce the risk of infection. Communication with mobile devices may facilitate monitoring test results.

Various examples have been described. These and other examples are within the scope of the following claims.

The invention claimed is:

1. A biological property testing apparatus, comprising:
   a housing;
   a testing module removably attachable to the housing, the testing module including:
      a base comprising a primary surface extending in a base plane,
      a first lancet station supported by the base and having a recessed portion recessed from the primary surface of the base, the first lancet station comprising:
         a first lancet,
         a lancet station housing supported by the recessed portion, the lancet station housing configured to support the first lancet, and
         a lancet cover that is movable between an un-depressed position in which the lancet cover covers the first lancet and a depressed position in which the first lancet protrudes through a first lancet aperture in the lancet cover,
      a first test strip channel provided in the base, the first test strip channel having a main channel portion extending generally parallel with the base plane, and an angled channel portion that forms an angle with the main channel portion between 5 degrees and 90 degrees, and
      a biological test strip that has a sample end and a meter connecting end, the biological test strip being housed in the first test strip channel with the meter connecting end extending from the main channel portion and the sample end extending from the angled channel portion; and
   a meter module attachable to the housing, the meter module including an input port configured to receive the meter connecting end of the biological test strip when the testing module and the meter module are attached to the housing.

2. The biological property testing apparatus of claim 1, wherein the housing includes a first side and a second side, the testing module and the meter module being attachable to the first side of the housing, the second side of the housing including adhesive to adhere the housing to a mobile device.

3. The biological property testing apparatus of claim 1, wherein the meter module includes a wireless transmitter to communicate a biological property test result to a mobile device.

4. The biological property testing apparatus of claim 1, further comprising a cover removably attachable to the housing, the cover being configured to cover the testing module and the meter module when the cover, the testing module, and the meter module are attached to the housing.

5. The biological property testing apparatus of claim 1, wherein the base further comprises a secondary surface opposite the primary surface and an edge surface extending between the primary surface and the secondary surface, and wherein a meter connecting end opening of the main channel portion of the test strip channel is formed in the edge surface of the base, and wherein a sample end opening of the angled channel portion of the test strip channel is formed in either the primary surface or the secondary surface of the base.

6. The biological property testing apparatus of claim 5, wherein the primary surface includes a sample cavity, and wherein the sample end opening is formed in the sample cavity.

7. The biological property testing apparatus of claim 1, wherein the first test strip channel comprises four walls defining a rectangular cross section, and wherein at least one of the four walls is integral with the base, and wherein at least one of the four walls is removable to facilitate positioning of the biological test strip.

8. The biological property testing apparatus of claim 1, wherein the testing module further includes:
a second lancet station supported by the base and comprising a second lancet; and
a second test strip channel provided in the base.

9. The biological property testing apparatus of claim 8, wherein the first lancet station is aligned with the first test strip channel, and wherein the second lancet station is aligned with the second test strip channel.

10. A biological property testing apparatus, comprising:
a testing module, the testing module including:
a base comprising a primary surface extending in a base plane, a secondary surface opposite the primary surface, and an edge surface extending between the primary surface and the secondary surface, the primary surface including a sample cavity,
a lancet station supported by the base and comprising a lancet,
a test strip channel provided in the base, the test strip channel having a main channel portion extending generally parallel with the base plane, and an angled channel portion that forms an angle with the main channel portion between 5 degrees and 90 degrees, wherein a meter connecting end opening of the main channel portion is formed in the edge surface of the base, and a sample end opening of the angled channel portion is formed in the sample cavity of the primary surface, and
a biological test strip that has a sample end and a meter connecting end, the biological test strip being housed in the test strip channel with the meter connecting end extending from the main channel portion and the sample end extending from the angled channel portion; and
a meter module attachable to the testing module, the meter module including an input port configured to receive the meter connecting end of the biological test strip when the testing module is attached to the meter module.

11. The biological property testing apparatus of claim 10, further comprising a housing, wherein the testing module and the meter module are attachable to the housing.

12. The biological property testing apparatus of claim 11, wherein the housing includes a first side and a second side, the testing module and the meter module being attachable to the first side of the housing, the second side of the housing including adhesive to adhere the housing to a mobile device.

13. The biological property testing apparatus of claim 10, wherein the angle formed by the main channel portion and the angled channel portion is between 5 degrees and 45 degrees.

14. The biological property testing apparatus of claim 10, wherein the main channel portion has a length of between 15 millimeters and 24 millimeters and the angled channel portion has a length of between 4 millimeters and 7 millimeters, wherein the main channel portion and the angled channel portion have a common width of between 5 millimeters and 9 millimeters, and wherein the angle formed by the main channel portion and the angled channel portion is between 5 degrees and 45 degrees.

15. The biological property testing apparatus of claim 10, wherein the test strip channel comprises a channel length, and wherein the channel length is between about 55% and about 70% of a test strip length of the biological test strip.

16. The biological property testing apparatus of claim 10, wherein the lancet station has a recessed portion recessed from the primary surface of the base, the lancet station comprising:
a lancet station housing supported by the recessed portion of the lancet station, the lancet station housing configured to support the lancet, and
a lancet cover that is movable between an un-depressed position in which the lancet cover covers the lancet and a depressed position in which the lancet protrudes through an aperture in the lancet cover.

17. The biological property testing apparatus of claim 10, wherein the meter module includes a wireless transmitter to communicate a biological property test result to a mobile device.

18. The biological property testing apparatus of claim 10, wherein the test strip channel comprises four walls defining a rectangular cross section, and wherein at least one of the four walls is integral with the base, and wherein at least one of the four walls is removable to facilitate positioning of the biological test strip.

19. A biological property testing apparatus, comprising:
a testing module, the testing module including:
a base comprising a primary surface extending in a base plane,
a first lancet station supported by the base and comprising a lancet,
a second lancet station supported by the base and comprising a second lancet,
a first test strip channel provided in the base, the first test strip channel having a main channel portion extending generally parallel with the base plane, and an angled channel portion that forms an angle with the main channel portion between 5 degrees and 90 degrees,
a second test strip channel provided in the base, and
a biological test strip that has a sample end and a meter connecting end, the biological test strip being housed in the first test strip channel with the meter connecting end extending from the main channel portion and the sample end extending from the angled channel portion; and
a meter module attachable to the testing module, the meter module including an input port configured to receive the meter connecting end of the biological test strip when the testing module is attached to the meter module.

20. The biological property testing apparatus of claim 19, wherein the first lancet station is aligned with the first test strip channel, and wherein the second lancet station is aligned with the second test strip channel.

21. The biological property testing apparatus of claim 19, further comprising a housing, wherein the testing module and the meter module are attachable to the housing.

22. The biological property testing apparatus of claim 21, further comprising a cover removably attachable to the housing, the cover being configured to cover the testing module and the meter module when the cover, the testing module, and the meter module are attached to the housing.

23. The biological property testing apparatus of claim 21, wherein the housing includes a first side and a second side, the testing module and the meter module being attachable to the first side of the housing, the second side of the housing including adhesive to adhere the housing to a mobile device.

24. The biological property testing apparatus of claim 19, wherein the meter module includes a wireless transmitter to communicate a biological property test result to a mobile device.

25. The biological property testing apparatus of claim 19, wherein the main channel portion has a length of between 15 millimeters and 24 millimeters and the angled channel portion has a length of between 4 millimeters and 7 millimeters, wherein the main channel portion and the angled channel portion have a common width of between 5 millimeters and 9 millimeters, and wherein the angle formed by the main channel portion and the angled channel portion is between 5 degrees and 45 degrees.

26. The biological property testing apparatus of claim 19, wherein the first test strip channel comprises a channel length, and wherein the channel length is between about 55% and about 70% of a test strip length of the biological test strip.

\* \* \* \* \*